United States Patent
Ales, III et al.

(10) Patent No.: US 7,700,821 B2
(45) Date of Patent: Apr. 20, 2010

(54) METHOD AND DEVICE FOR DETERMINING THE NEED TO REPLACE AN ABSORBENT ARTICLE

(75) Inventors: Thomas Michael Ales, III, Neenah, WI (US); Andrew Mark Long, Appleton, WI (US); Meghan Elizabeth Collins, Palatine, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 232 days.

(21) Appl. No.: 11/897,605

(22) Filed: Aug. 30, 2007

(65) Prior Publication Data

US 2009/0062758 A1    Mar. 5, 2009

(51) Int. Cl.
*A61F 13/15*  (2006.01)
*A61F 13/20*  (2006.01)

(52) U.S. Cl. .................................................. 604/361
(58) Field of Classification Search ................ 604/361
See application file for complete search history.

(56) References Cited

U.S. PATENT DOCUMENTS

| | | | |
|---|---|---|---|
| 4,100,324 A | 7/1978 | Anderson et al. | |
| 4,704,116 A | 11/1987 | Enloe | |
| 4,940,464 A | 7/1990 | Van Gompel et al. | |
| 5,258,745 A | 11/1993 | Colling | |
| 5,284,703 A | 2/1994 | Everhart et al. | |
| 5,350,624 A | 9/1994 | Georger et al. | |
| 5,486,166 A | 1/1996 | Bishop et al. | |
| 5,490,846 A | 2/1996 | Ellis et al. | |
| 5,557,263 A | 9/1996 | Fisher et al. | |
| 5,760,694 A | 6/1998 | Nissim et al. | |
| 5,766,389 A | 6/1998 | Brandon et al. | |
| 5,790,035 A * | 8/1998 | Ho .......................... | 340/573.5 |
| 5,820,973 A | 10/1998 | Dodge, II et al. | |
| 5,908,411 A | 6/1999 | Matsunari | |
| 6,246,330 B1 | 6/2001 | Nielsen | |
| 6,645,190 B1 | 11/2003 | Olson et al. | |
| 7,250,547 B1 * | 7/2007 | Hofmeister et al. .......... | 604/361 |
| 2004/0078219 A1 | 4/2004 | Kaylor et al. | |
| 2004/0100376 A1 | 5/2004 | Lye et al. | |
| 2004/0220538 A1 | 11/2004 | Panopoulos | |

(Continued)

FOREIGN PATENT DOCUMENTS

JP    2005-000602 A    1/2005

(Continued)

*Primary Examiner*—Hezron Williams
*Assistant Examiner*—Nathaniel Kolb
(74) *Attorney, Agent, or Firm*—Randall W. Fieldhack

(57) ABSTRACT

A wetness monitoring system is provided for an absorbent article, the wetness monitoring system including a signaling device including a counter to count the number of discrete insults, a timer to monitor the elapsed time that the article has been worn, and an alarm to indicate that the number of discrete insults has reached an insult limit or that the elapsed time has reached an elapsed time limit, whichever occurs first. The signaling device can be adapted to indicate one of first, second, and third conditions, the first condition being that the number of discrete insults has reached an insult limit, the second condition being that the elapsed time has reached an elapsed time limit, and the third condition being the first to occur of either of the first and second conditions, and wherein the condition to be indicated is selected by the wearer or by a caregiver.

19 Claims, 6 Drawing Sheets

U.S. PATENT DOCUMENTS

| | | | |
|---|---|---|---|
| 2007/0049883 A1 | 3/2007 | Ales et al. | |
| 2007/0049885 A1* | 3/2007 | Phillips | 604/361 |
| 2007/0083174 A1 | 4/2007 | Ales et al. | |
| 2007/0142799 A1 | 6/2007 | Ales et al. | |
| 2007/0270774 A1* | 11/2007 | Bergman et al. | 604/361 |

FOREIGN PATENT DOCUMENTS

| | | |
|---|---|---|
| WO | WO 00/37009 A2 | 6/2000 |
| WO | WO 2007/070267 A1 | 6/2007 |

* cited by examiner

METHOD AND DEVICE FOR DETERMINING THE NEED TO REPLACE AN ABSORBENT ARTICLE

BACKGROUND

The present invention relates generally to a method of detecting the presence of an insult in an absorbent article while it is being worn by a wearer and a monitoring system for performing the method.

Absorbent articles associated with wetness indicators have been proposed to signal to a caregiver when the absorbent article has been insulted. One way of monitoring a toilet-training child is by using a system that detects a change in an electrical property of the undergarment when the electrical property is a function of the wetness of the undergarment. For example, the electrical property may be resistance, conductance, impedance, capacitance or any other parameter which varies as the wetness of the undergarment varies. For example, a pair of spaced apart parallel conductors may be situated within the absorbent material of the undergarment. These conductors are in electrical contact with the absorbent material of the undergarment and are connected to a sensing circuit for monitoring the electrical property, the circuit includes a power source, such as a battery. For example, the circuit may comprise a voltage divider for detecting resistance between the conductors. The output of the circuit is an analog output voltage that corresponds to a resistance value. When the undergarment is dry, the resistance between the conductors is extremely high and relatively infinite, appearing as an open circuit. When the undergarment is wet, more particularly when the absorbent material of the undergarment between the conductors becomes wet, the resistance of the undergarment at that area drops to a relatively lower value because urine acts as a conductor.

Accordingly, in a conventional system a sensor monitors the resistance between the conductors and compares resistance values to a predetermined and fixed threshold resistance value. If a resistance value is less than the threshold resistance value, then the sensing circuit (herein sensor) sends a signal to an alarm device, which informs the caregiver and/or the wearer that the wearer has urinated. For example, the alarm device may be a device for producing an auditory signal, such as a song, a visual signal, such as a light, or a tactile signal, such as a change in temperature.

For potty training and enuretic use of absorbent articles, it is typically useful for the caregiver and/or user to know immediately when an absorbent article has been insulted to allow for corrective action and the training process. For other uses of absorbent articles, the caregiver can benefit from knowing how many times the absorbent article has been insulted without necessarily being required to change and discard the absorbent article. This can be the case for newborns and infants. Even if the absorbent article is insulted with urine, caregivers often will not change the absorbent article until it contains a bowel movement or the absorbent article feels saturated with urine. Especially with newborns, the urine insults are typically very frequent and in small amounts. Regardless, after some time the caregiver will need to change the absorbent article for skin health reasons.

SUMMARY

This disclosure solves these problems by providing a solution that allows a caregiver to determine when an absorbent article should be changed based on the number of insults it has received, the elapsed time since it was donned, or both. This disclosure includes an article and method that allows the caregiver to know how many times the absorbent article has been insulted while alarming at a pre-set insult limit. This disclosure also includes an article and method that allows the caregiver to know how much time has elapsed since the absorbent article was donned while alarming at a pre-set elapsed time limit. The article and method of this disclosure strikes a balance between reducing the number of absorbent article changes to accrue economic and convenience benefits, and frequently changing the absorbent article for skin health benefits.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

Figure 1:
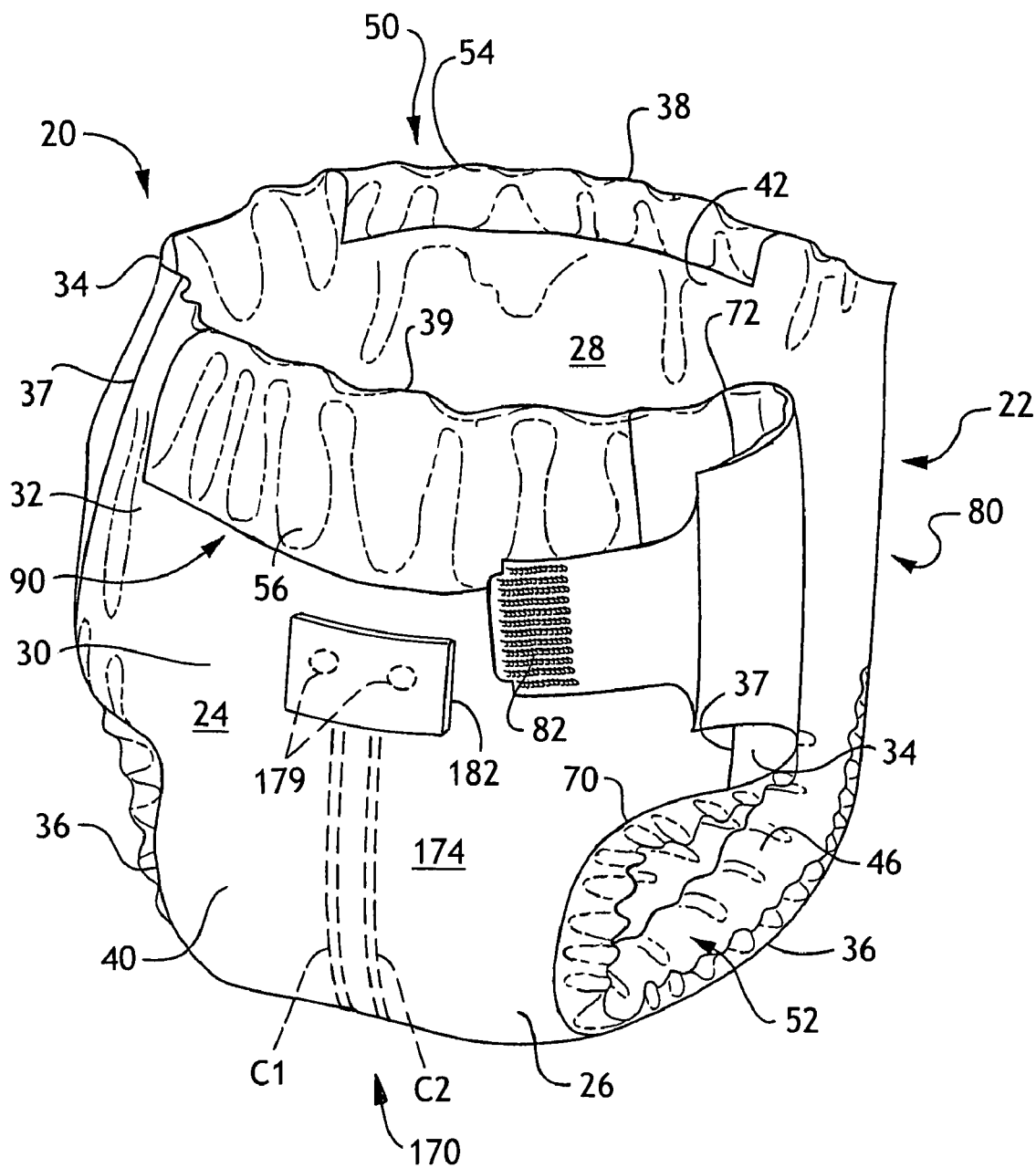
FIG. 1 is a rear perspective view of one aspect of an absorbent article.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

Newborns and infants exhibit urination patterns that are different from those of children who are potty training. Newborns and infants will often insult a product 20 mL at a time with only minutes, such as 10-20 minutes, between urinations. Similar behavior can be displayed by users of adult incontinence products as well. To track such urination behavior a wetness sensing device can be enabled with higher order algorithms to process the resistance data that is captured from the absorbent article when the absorbent article and wetness sensing device are in use, as described in more detail herein and in co-pending and co-assigned U.S. patent application Ser. No. 11/611,435, filed on Dec. 15, 2006, by Ales, et al., which is incorporated herein by reference to the extent it is consistent (i.e., not in conflict) herewith.

As used herein, wearer, baby, newborn, and infant refer to the subject who has donned the absorbent article. Caregiver refers to the parent or other person who is taking care of the infant, including changing the absorbent article. User can refer to either the caregiver or the wearer of the absorbent article, depending on the context of its use and the capabilities needed to use the object in question.

Figure 2:
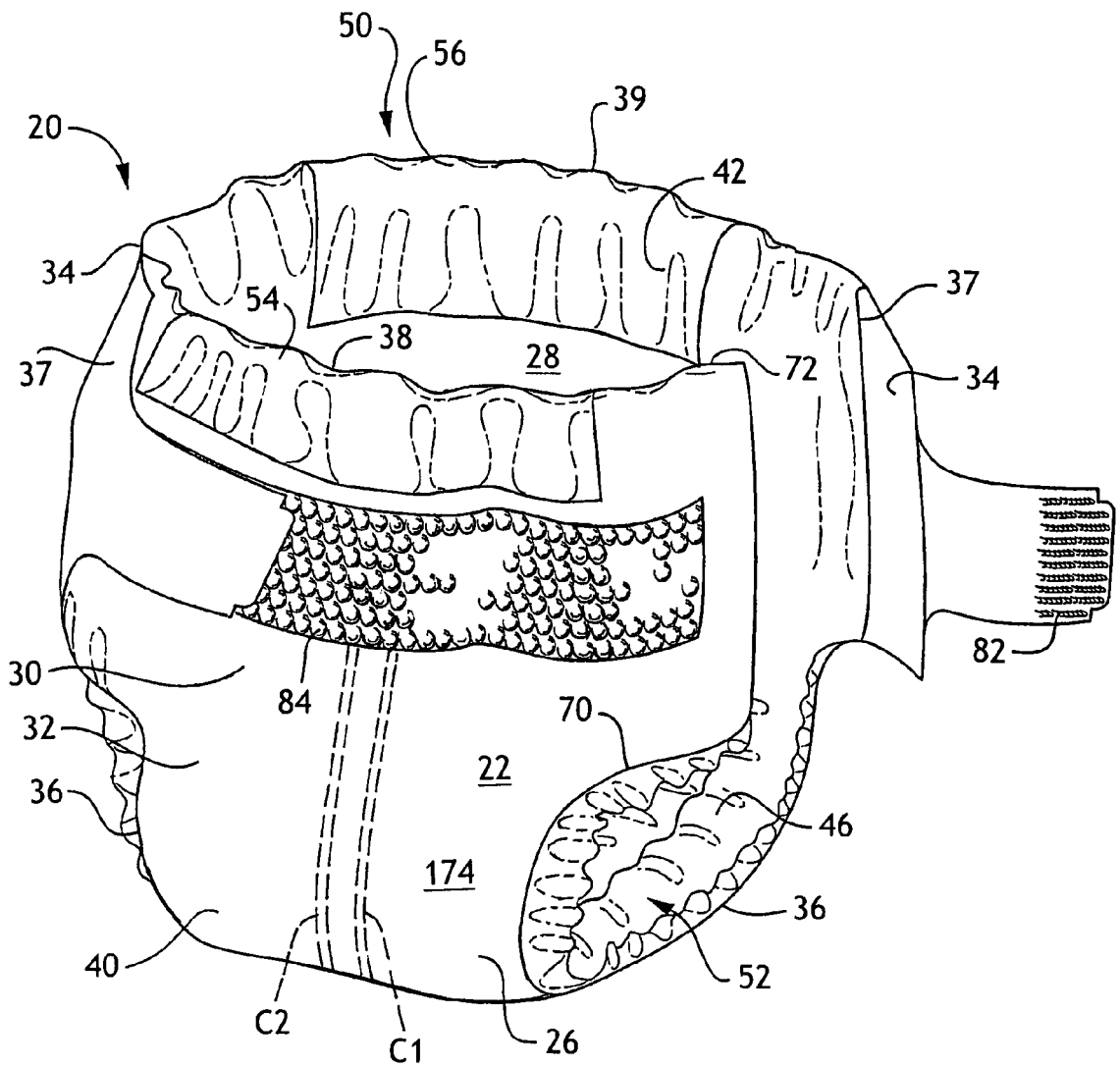
FIG. 2 is a front perspective view of the absorbent article illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the diaper 20 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
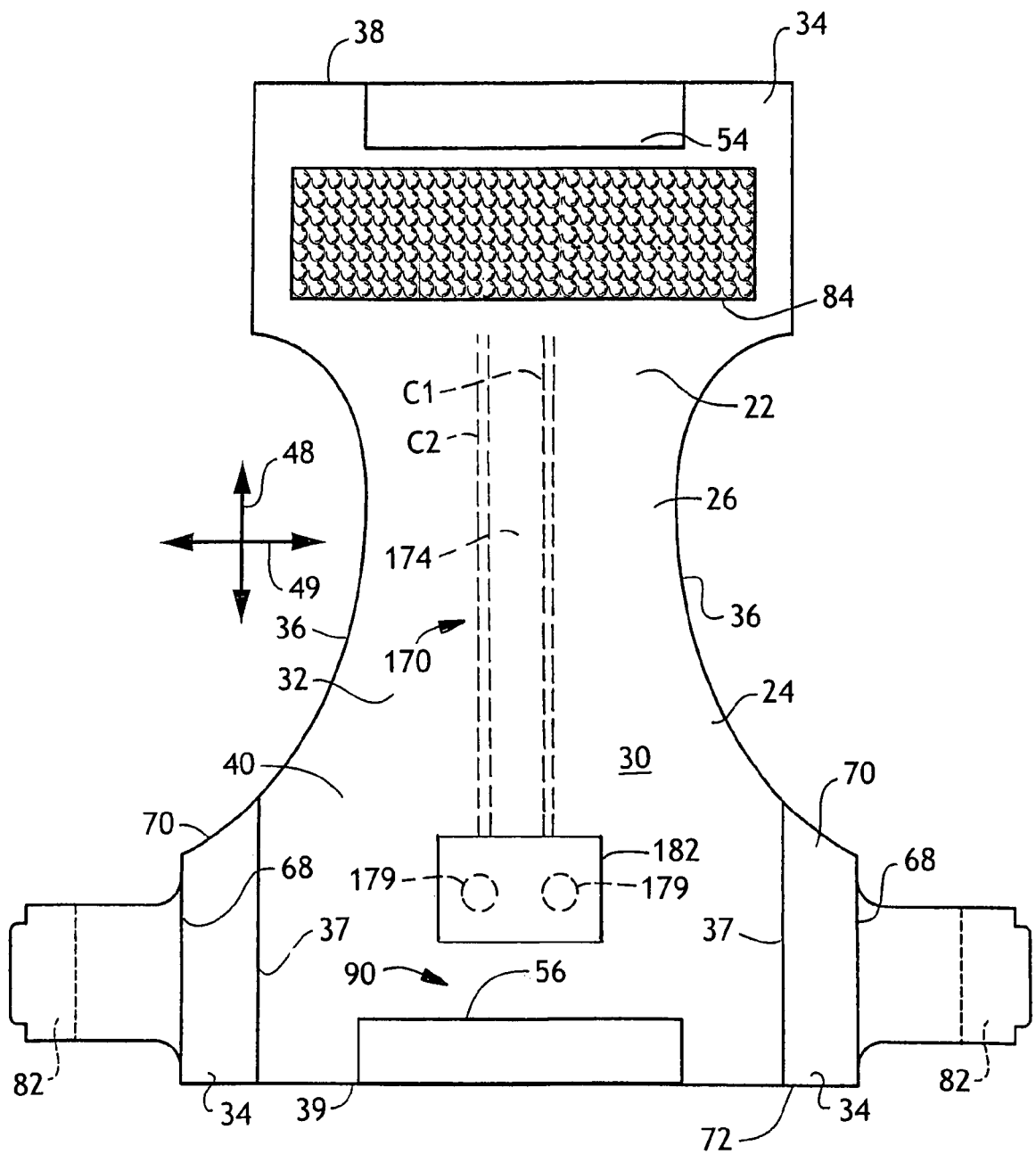
FIG. 3 is a plan view of the absorbent article shown in FIG. 1 with the article in an unfastened, unfolded and laid flat condition showing the surface of the article that faces away from the wearer.
Figure 4:
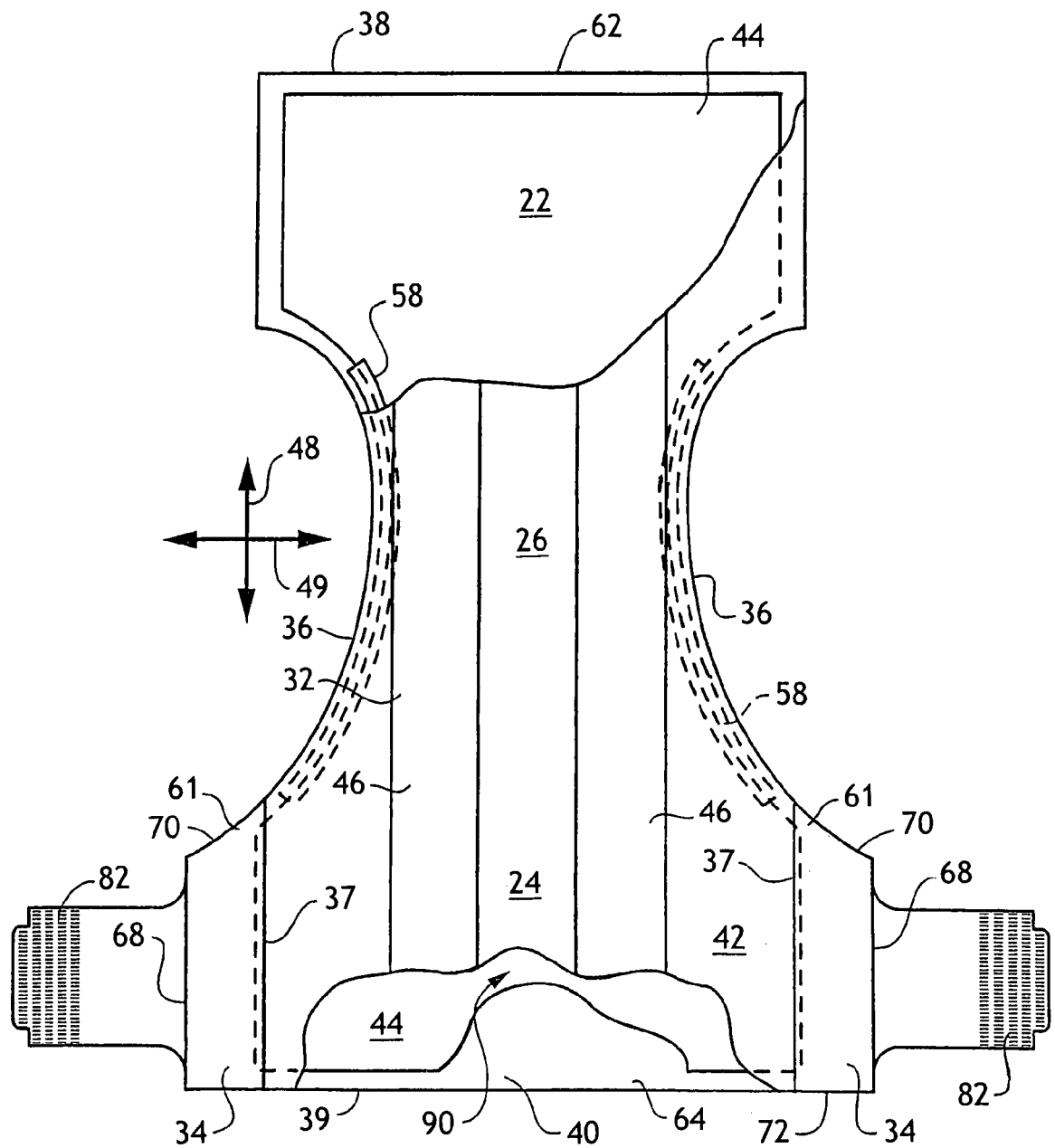
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some aspects, the absorbent article 20 may further include a surge management layer 60 that may be optionally located adjacent the absorbent structure 44 and attached to various components in the article 20, such as the absorbent structure 44 or the bodyside liner 42, by methods known in the art, such as by using an adhesive. A surge management layer 60 helps to decelerate and diffuse surges or gushes of liquid that may be rapidly introduced into the absorbent structure of the article. Desirably, the surge management layer 60 can rapidly accept and temporarily hold the liquid prior to releasing the liquid into the storage or retention portions of the absorbent structure. Examples of suitable surge management layers 60 are described in U.S. Pat. No. 5,486,166 issued Jan. 23, 1996 to David F. Bishop et al. and U.S. Pat. No. 5,490,846 issued Feb. 13, 1996 to Clifford J. Ellis et al. Other suitable surge management materials are described in U.S. Pat. No. 5,820,973 issued Oct. 13, 1998 to Richard N. Dodge II et al. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative aspect, the elastic side panels may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels are releasably attachable to the front region 22 of the article 20 by the fastening system. It should be understood, however, that in other aspects, the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material, or the like. One skilled in the art will recognize that the shape, density, and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the aspect shown in the figures, the fastening components 82 are attached to the side panels 34 along the edges 68. In this aspect, the fastening components 82 are not elastic or extendable. In other aspects, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded-carded webs or foams provided by elastomeric or polymeric materials. The outer cover 40, for instance, can be a single layer of a liquid impermeable material, or alternatively can be a multi-layered laminate structure in which at least one of the layers is liquid impermeable. In other aspects, however, it should be understood that the outer cover may be liquid permeable. In this aspect, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40, when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., U.S.A., and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394 and Favor 9543 superabsorbents are available from DeGussa Superabsorbers, located at Parsippany, N.J., U.S.A.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

The absorbent article 20 of the present invention includes a wetness monitoring system for detecting the presence of urine (broadly, an insult) within the absorbent article 20. Although the wetness monitoring system may take on other configurations, this particular configuration of the system monitors an electrical characteristic of the absorbent article 20 and determines whether the wearer has urinated in the absorbent article 20 using such electrical characteristic. After detection of urine, the system informs a caregiver and/or a wearer of the presence of the urine by generating an insult alarm. The alarm may be, for example, either an auditory signal, such as a song, or a tactile signal, such as temperature change, or a visual signal, such as a blinking light, as long as the alarm is perceptible to the wearer, a caregiver, or both. It is understood that the system may include a device for sending a wireless signal to a remote auditory, visual, tactile or other sensory alarm. To conserve battery life in either the signaling device or in a remote indication means, the caregiver or remote indication means can periodically query the signaling device or the remote indication means, as appropriate, for the number of insults or for the amount of elapsed time.

In one particularly suitable embodiment, shown best in FIG. 2, one example of the wetness monitoring system is generally indicated by reference numeral 170. The monitoring system 170 includes a sensor for detecting the electrical property (e.g., resistance R) of the article. The sensor includes a pair of spaced apart generally parallel conductors C1, C2 disposed within the absorbent article 20 that define a monitoring area 174 of the absorbent article 20 disposed between the conductors. The conductors C1, C2 may be constructed of any material that is generally electrically conductive. For example, the conductors may be constructed of metal strips (e.g., aluminum strips), metal films, coated films, conductive polymers, conductive inks, or conductive threads. Other conductors are within the scope of this invention. The conductors C1, C2 extend longitudinally from the front region 22, through the crotch region 26, to the back region 24 of the absorbent article 20. The conductors C1, C2 are disposed with the absorbent structure 44 between the absorbent structure 44 and the bodyside liner 42, although the conductors may be disposed at other locations without departing from the scope of this invention.

Figure 5:
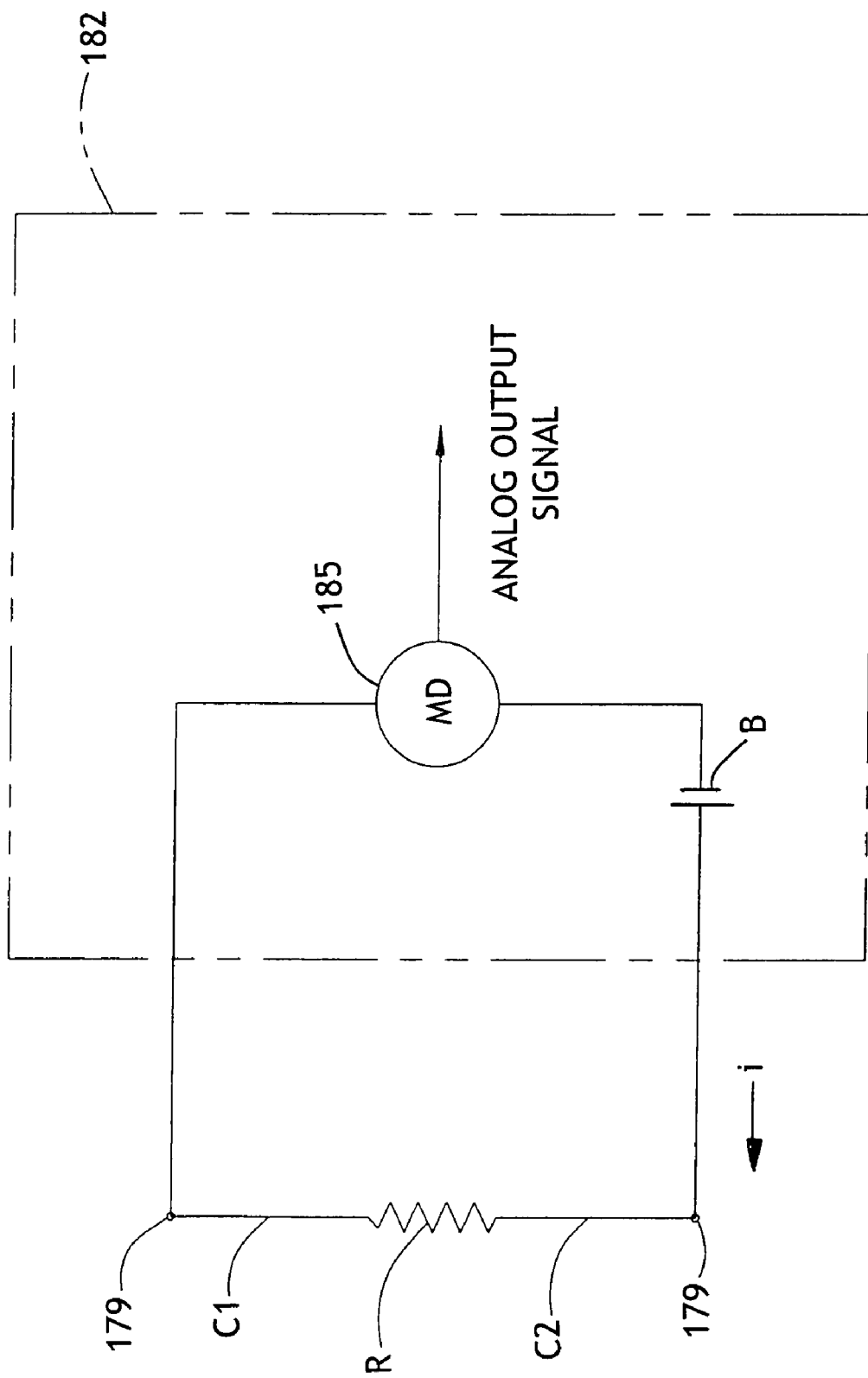
FIG. 5 is a schematic of a wetness sensing circuit.

As best illustrated in FIGS. 1 and 5, current i from a current source B runs through the conductors C1, C2 of the sensor. The current source i may be a direct current source such as a battery or an alternating current source. In the illustrated embodiment, the conductors C1, C2 are electrically connected to the current source by way of electrically conductive snap fasteners 179. Other ways of electrically connecting the conductors to the current source are within the scope of this invention. Each corresponding end of each conductor C1, C2 is connected to a conductive snap fastener 179 located in the back region 24 of the absorbent article 20. Alternatively, the conductive snap fastener 179 may be located in the front region 22, or in other locations on the absorbent article 20. A housing 182 that houses the current source i has corresponding conductive snap fasteners for engaging the conductive snap fasteners 179 and securing the housing 182 to the absorbent article 20. In addition to the current source i, the housing 182 of the present embodiment also houses the remaining components of the wetness monitoring system 170 that will be described hereinafter, although it is contemplated that the housing 182 may include only some or none of the remaining components. In the illustrated embodiment the housing 182 is releasably secured to the absorbent article 20 by way of the snap fasteners 179, although it is understood that the housing may be releasably secured by other means or permanently secured to the absorbent article 20 without departing from the scope of this invention.

A measuring device 185 of the sensor measures an electrical property of the monitoring area 174 of the absorbent article 20. In one embodiment, the resistance R of the monitoring area 174 of the absorbent article 20 is measured. Because the conductors C1, C2 are spaced apart, current from the current source i must pass through the monitoring area 174 to complete the circuit. The monitoring area 174 acts essentially as a resistor, as indicated by reference character R. When the monitoring area 174 is dry (e.g., before the presence of an insult), the resistance of the monitoring area is relatively high, for example, some resistance above 200 k$\Omega$. When the monitoring area 174 is wetted, for example by an insult, its resistance drops, for example, to some resistance less than 200 k$\Omega$ because of the electrically-conductive nature of urine.

In another embodiment, the conductance of the monitoring area 174 of the absorbent article 20 is measured. As stated above, urine is electrically conductive, and the absorbent article 20 generally is not electrically conductive. Therefore, when the monitoring area 174 of the absorbent article 20 is wetted, its conductance is greater than when it is dry. Other electrical properties of the absorbent article 20, including impedance, may be measured without departing from the scope of this invention.

Additional technical detail is provided in co-pending and co-assigned U.S. patent application Ser. No. 11/611,435, filed on Dec. 15, 2006, by Ales, et al., which is incorporated herein by reference to the extent it is consistent (i.e., not in conflict) herewith.

Figure 6:
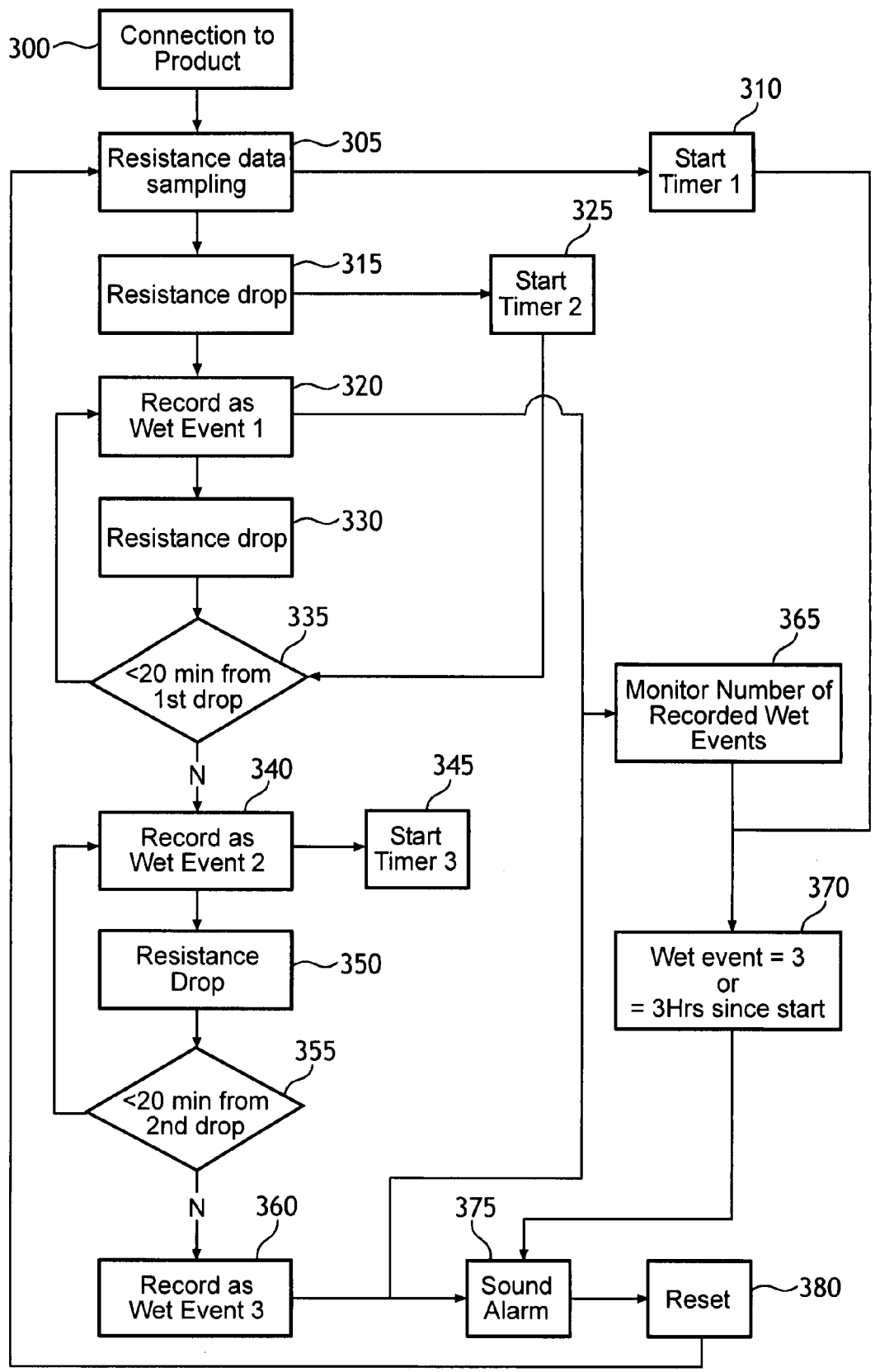
FIG. 6 is a block diagram for one aspect of the disclosure employing the absorbent article of FIGS. 1-4.

To track the urination behavior of newborns and infants, a wetness sensing device can be enabled with higher order algorithms to process the resistance data that is captured from the absorbent article when the absorbent article and wetness sensing device are in use. FIG. 6 provides an exemplary illustration of such an algorithm. The signaling device is connected 300 to the absorbent article product and begins to sample resistance data 305. At the same time, Timer1 is started 310 to record the total time for which the absorbent article is worn by the wearer. Upon a urine insult to the absorbent article, the resistance drops and such resistance drop is sensed by the signaling device 315. The signaling device records the insult as Wet Event1 320 and starts Timer2 325 to record the time between successive insults.

When the signaling device senses a second resistance drop 330 indicating a second insult, the signaling device reads the elapsed time recorded by Timer2 335. If the elapsed time between the first and second insults is less than 20 minutes, then the signaling device considers the second insult to be a continuation of the first insult 320. It should be noted that there is no limit to the number of insults that can occur in such a pre-selected time period. For example, if one, two, three, or more insults occur within that 20 minutes, they can still be counted as one insult. If the elapsed time between the first and second insults is equal to or greater than 20 minutes, the signaling device considers the second insult to be a separate event and records the insult as Wet Event2 340. At the same time the signaling device records a Wet Event2 340, the signaling device also starts Timer3 345 to record the elapsed time between the second and third insults.

When the signaling device senses a third resistance drop 350 indicating a third insult, the signaling device reads the elapsed time recorded by Timer3 355. If the elapsed time between the second and third insults is less than 20 minutes, then the signaling device considers the third insult to be a continuation of the second insult 340. If the elapsed time between the second and third insults is equal to or greater than 20 minutes, the signaling device considers the third insult to be a separate event and records the insult as Wet Event3 360.

The signaling device also monitors the number of recorded Wet Events 365. When the signaling device determines that the number of Wet Events equals three or that three hours have elapsed on Timer1 370 (in other words, the absorbent article has been worn for three hours), the signaling device sounds an alarm 375. Removing the signaling device from the absorbent article and placing the signaling device on a new absorbent article resets all of the timers and counters 380.

In this example, the three insults leading to an alarm is the insult limit for the signaling device. The insult limit can be preselected by the manufacturer or can be selectable by the user of the signaling device. Where the insult limit is other than three, the flowchart of FIG. 6 can be modified to accommodate the change in insult limit. The three-hour elapsed time leading to an alarm is the elapsed time limit for the signaling device. The elapsed time limit can be preselected by the manufacturer or can be selectable by the user of the signaling device. The 20-minute time to determine whether successive insults will be recorded as separate Wet Events is a single insult time and can also be preselected by the manufacturer or can be selectable by the user of the signaling device.

In another aspect of the present disclosure, Timer1 or a separate Timer1A may be started upon the first insult to measure the elapsed time the absorbent article is being worn after the first insult. Some caregivers and/or wearers may find this elapsed time more relevant for skin health purposes.

In other aspects of the present disclosure, the signaling device can be adapted to provide an alarm when the insult limit has been met, when the elapsed time limit has been met, or when the first of these to occur is satisfied. In one aspect, which alarm configuration or configurations are employed can be selected by the user. In addition, the signaling device can be configured to provide a choice of alarms for either the insult limit or the elapsed time limit or both, with the configuration to be selected by either the manufacturer or the user. The signaling device can also be configured to provide different alarms for the insult limit and for the elapsed time limit.

In other aspects of the present disclosure, the signaling device can include a display of the number of insults, a display of the elapsed time, or both. The display may be an LCD display, a series of LED lights, or any other display type suitable for displaying such information to a user.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole and in part. Furthermore, those of ordinary skill in the art will appreciate that the foregoing description is by way of example only, and is not intended to limit the disclosure so further described in such appended claims.

What is claimed is:

1. A wetness monitoring system for an absorbent article to be worn by a wearer, the wetness monitoring system comprising a signaling device including a counter to count the number of discrete insults to the absorbent article, a timer to monitor the elapsed time that the article has been worn, and an alarm to indicate one of first, second, and third conditions, wherein the first condition is that the number of discrete insults has reached an insult limit, the second condition is that the elapsed time has reached an elapsed time limit, and the third condition is the first to occur of either of the first and second conditions, and wherein the condition to be indicated is selected by the wearer or by a caregiver.

2. The wetness monitoring system of claim 1, wherein the alarm includes providing a signal perceptible to a caregiver.

3. The wetness monitoring system of claim 2, wherein the alarm is an audio signal.

4. The wetness monitoring system of claim 2, wherein the alarm is a visual signal.

5. The wetness monitoring system of claim 2, wherein the alarm is selectable by the caregiver or wearer from a plurality of alarms.

6. The wetness monitoring system of claim 1, wherein the insult limit is selectable by the wearer or by a caregiver.

7. The wetness monitoring system of claim 1, wherein the elapsed time limit is selectable by the wearer or by a caregiver.

8. The wetness monitoring system of claim 1, wherein the counter counts successive insults as one discrete insult if the successive insults occur within a single insult time.

9. The wetness monitoring system of claim 8, wherein the single insult time is selectable by the wearer or by a caregiver.

10. The wetness monitoring system of claim 1, wherein the counter and the timer are adapted to be reset to zero.

11. The wetness monitoring system of claim 1, wherein the signaling device displays the number of insults.

12. The wetness monitoring system of claim 1, wherein the signaling device displays the elapsed time.

13. The wetness monitoring system of claim 1, wherein the elapsed time is measured from a first insult.

14. A method of determining the need to replace an absorbent article being worn by a wearer, the method comprising:
    counting the number of discrete insults to the absorbent article;
    monitoring the elapsed time that the article has been worn;
    indicating one of first, second, and third conditions, wherein the first condition being that the number of discrete insults has reached an insult limit, the second condition being that the elapsed time has reached an elapsed time limit, and the third condition being the first to occur of either of the first and second conditions, and wherein the condition to be indicated is selected by the wearer or by a caregiver.

15. The method of claim 14, wherein indicating includes providing an alarm perceptible to a caregiver.

16. The method of claim 14, wherein indicating includes a first alarm that the number of discrete insults has reached the insult limit and a second alarm that the elapsed time has reached the time limit, and wherein the first alarm is different from the second alarm.

17. The method of claim 14, wherein monitoring includes displaying the elapsed time.

18. A wetness monitoring system for an absorbent article to be worn by a wearer, the wetness monitoring system comprising a signaling device including a counter to count the number of discrete insults to the absorbent article and a timer to monitor the elapsed time that the article has been worn, wherein the signaling device is adapted to indicate one of first, second, and third conditions, the first condition being that the number of discrete insults has reached an insult limit, the second condition being that the elapsed time has reached an elapsed time limit, and the third condition being the first to occur of either of the first and second conditions, and wherein the condition to be indicated is selected by the wearer or by a caregiver.

19. The wetness monitoring system of claim 18, wherein the signaling device indicates using an alarm perceptible to a caregiver.

* * * * *